United States Patent [19]

Sprague et al.

[11] Patent Number: 4,499,292

[45] Date of Patent: Feb. 12, 1985

[54] 7-OXABICYCLOHEPTANE PROSTAGLANDIN INTERMEDIATES AND METHOD FOR PREPARING SAME

[75] Inventors: Peter W. Sprague, Pennington; James E. Heikes, East Windsor, both of N.J.

[73] Assignee: E. R. Squibb & Sons, Inc., Princeton, N.J.

[21] Appl. No.: 494,233

[22] Filed: May 13, 1983

[51] Int. Cl.³ .............................................. C07D 307/88
[52] U.S. Cl. .................................................... 549/459
[58] Field of Search ......................................... 549/459

[56] References Cited

U.S. PATENT DOCUMENTS 4,143,054  3/1979  Sprague ............................. 549/459
4,257,962  3/1981  Szabo et al. ........................ 549/465

FOREIGN PATENT DOCUMENTS 4493  10/1979  European Pat. Off. .

OTHER PUBLICATIONS

Orchin et al., The Vocabulary of Organic Chem., Wiley Publishers, pp. 144, 122, 130 and 131, (1980).
Sprague et al., Adv. in Prost. and Thromboxane Research, vol. 6, Raven Press., (1980), pp. 493–496.
Mitra, The Synthesis of Prostaglandins, Wiley, (1977), p. 12.

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

Optically active 7-oxabicyclopheptane prostaglandin intermediates are provided having the general structure

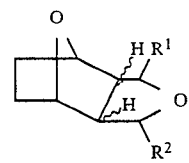

wherein one of $R^1$ and $R^2$ is

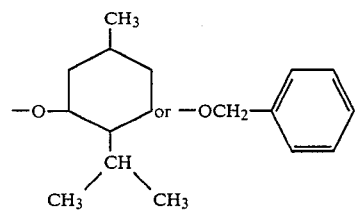

and the other is hydrogen.

A method for preparing the above intermediates is also provided.

15 Claims, No Drawings

7-OXABICYCLOHEPTANE PROSTAGLANDIN INTERMEDIATES AND METHOD FOR PREPARING SAME

FIELD OF THE INVENTION

The present invention relates to optically active intermediates for use in preparing 7-oxabicycloheptane prostaglandin analogs and to a method for preparing such intermediates.

BACKGROUND OF THE INVENTION

U.S. Pat. No. 4,143,054 to Sprague dated Mar. 6, 1979 discloses 7-oxabicycloheptane and 7-oxabicycloheptene prostaglandin analogs which are prepared by the following methods.

In a first method maleic anhydride is made to react with an unsubstituted or substituted furan of the formula

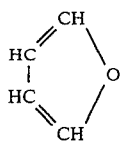

to form a compound of the formula

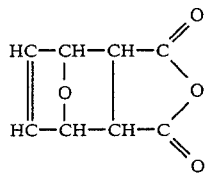

which is reduced to form

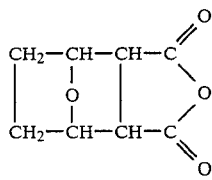

The above compound is then further reduced to form

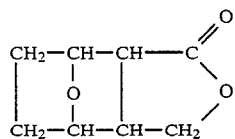    A

Treatment of the above compound with diisobutylaluminum hydride or diisobutylborane yields

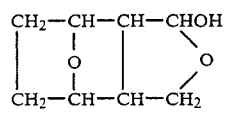    B

Submitting compound A to Wittig reaction conditions produces

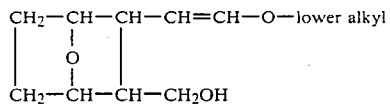    C

Compound C is then acylated and then hydrolyzed to form the aldehyde

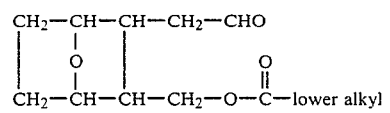    D

All of the above compounds are in the form of racemic mixtures.

Aldehyde D is subjected to a Wittig reaction to form a compound of the structure

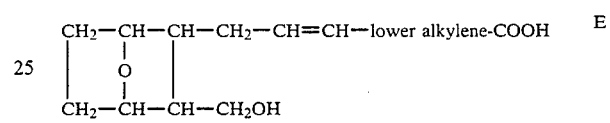    E which is esterified to form the corresponding lower alkyl ester. The hydroxymethyl group in the 3-position of the ester is then oxidized to obtain the aldehyde

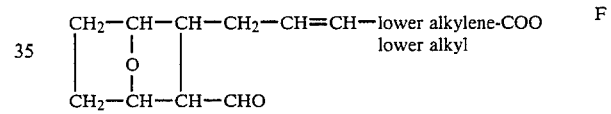    F

Aldehyde F which is in the form of a racemic mixture is employed to form 7-oxabicycloheptane prostaglandin analogs.

BRIEF DESCRIPTION OF THE INVENTION

In accordance with the present invention, a method is provided for forming the aldehyde F also depicted graphically as

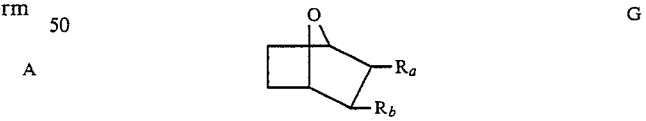    G wherein one of $R_a$ and $R_b$ is —$CH_2$—CH=CH— lower alkylene —COO lower alkyl and the other is —CHO in the form of its optically active isomer as opposed to a racemic mixture of two enantiomers as disclosed by Sprague in U.S. Pat. No. 4,143,054. The optically active aldehyde F(a) is then employed to form optically active 7-oxabicycloheptane prostaglandin analogs, for example, using the technique described by Sprague in U.S. Pat. No. 4,143,054.

In carrying out the method of the invention as described hereinafter several novel optically active intermediates are formed having the following formula

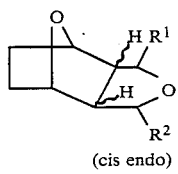

(cis endo)

wherein one of R¹ and R² is

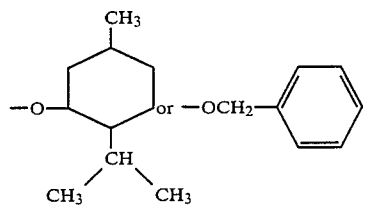

and the other is hydrogen, and includes the following compounds:

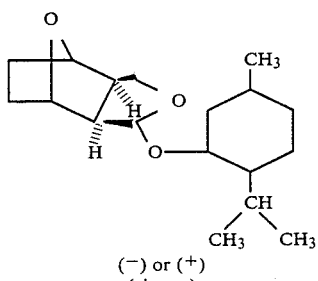  I I (−) or (+)
(cis exo)
[3aR—[1-(1R,2S,5R),3aα,4α,7α,7aα]]-Octahydro-1-[[5-methyl-2-(1-methylethyl)cyclohexyl]oxy]-4,7-epoxyisobenzofuran

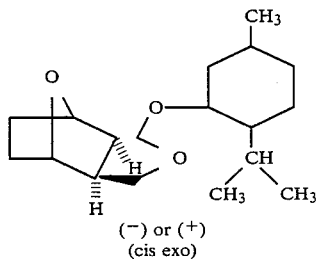 III (−) or (+)
(cis exo)
[3aS—[1-(1R,2S,5R),3aα,4α,7α,7aα]]-Octahydro-1-[[5-methyl-2-(1-methylethyl)cyclohexyl]oxy]-4,7-epoxyisobenzofuran

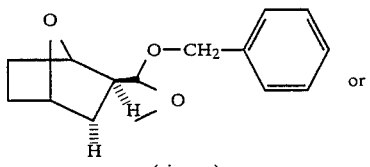 IV (cis exo)
[3aS—(3aα,4α,7α,7aα)]-Octahydro-1-benzyloxy-4,7-epoxyisobenzofuran

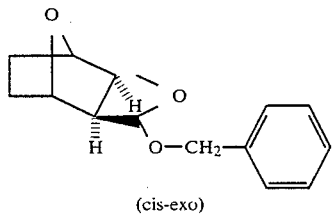 IVa (cis-exo)

-continued
[3aR—(3aα,4α,7α,7aα)]-Octahydro-1-benzyloxy-4,7-epoxyisobenzofuran

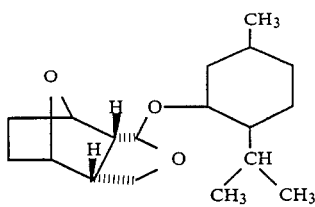 V (−) or (+)
(cis endo)
[3aR—[1-(1R,2S,5R),3aα,4β,7β,7aα]]-Octahydro-1-[[5-methyl-2-(1-methylethyl)cyclohexyl]oxy]-4,7-epoxyisobenzofuran

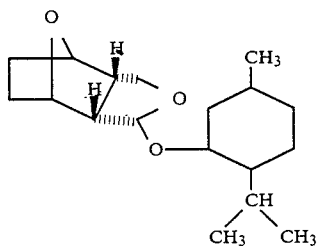 VI (−) or (+)
(cis endo)
[3aS—[1-(1R,2S,5R),3aα,4β,7β,7aα]]-Octahydro-1-[[5-methyl-2-(1-methylethyl)cyclohexyl]oxy]-4,7-epoxyisobenzofuran

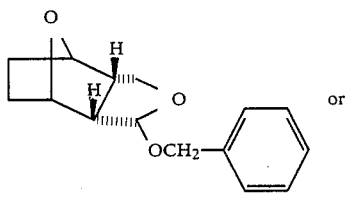 VII (cis endo)
[3aS—(3aα,4β,7β,7aα)]-Octahydro-1-benzyloxy-4,7-epoxyisobenzofuran

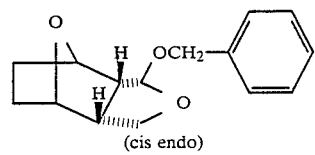 VIIa (cis endo)
[3aR—(3aα,4β,7β,7aα)]-Octahydro-1-benzyloxy-4,7-epoxyisobenzofuran The method of the present invention for forming optically active or chiral intermediates for use in preparing optically active 7-oxabicycloheptane prostaglandin analogs may be summarized in the following reaction sequence.

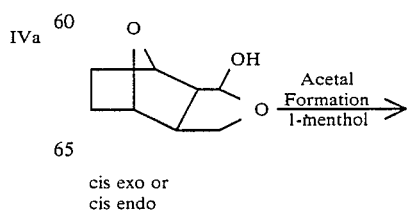

cis exo or
cis endo

-continued

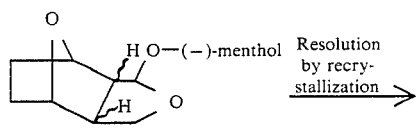

III (or V)

+

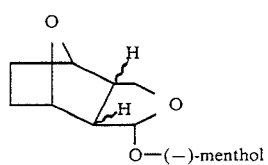

II (or VI)

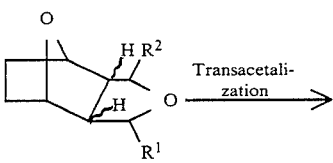 →Transacetalization→

(one of $R^1$ or $R^2$ is
—O—(—)-menthol and the
other is H) (optically active)
II or III
(or V or VI)

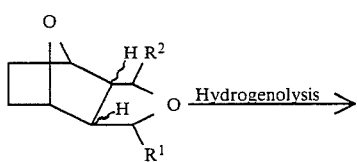 →Hydrogenolysis→

(one of $R^1$ or $R^2$ is —O—CH$_2$— [phenyl]

and the other is H)
(optically active)
IV or VII

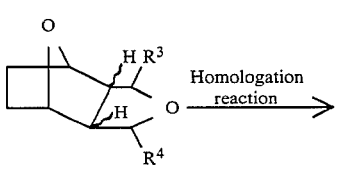 →Homologation reaction→

(one of $R^3$ and
$R^4$ is OH and the
other is H)
(optically active)
J

-continued

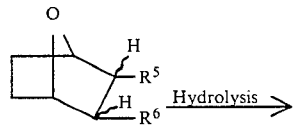 →Hydrolysis→

(one of $R^5$ or $R^6$ is
CH$_2$OH and the other is
—CH=CH—OCH$_3$)
(optically active)
K

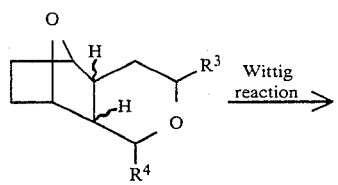 →Wittig reaction→

(wherein $R^3$ is OH and $R^4$
is H)
(optically active)
L

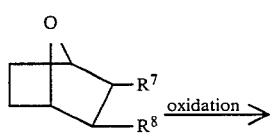 →oxidation→

(one of $R^7$ and $R^8$ is
—CH$_2$—CH=CH—lower alkylene-COCH$_3$
and the other is —CH$_2$OH)
(optically active)
M

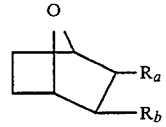

(one of $R_a$ and $R_b$ is
—CH$_2$—CH=CH—lower alkylene-CO$_2$CH$_3$
and the other is —CHO)
(optically active)
N The reaction sequence for preparing the optically active antipodes or mirror images of compounds of formulae II, III and IV, namely compounds of formulae V, VI and VII, respectively, may be prepared following the above reaction sequence except that d-menthol is employed in place of the corresponding l-isomer.

DETAILED DESCRIPTION OF THE INVENTION

The method of the invention is an advance over prior art methods for forming optically active 7-oxabicycloheptane prostaglandin analogs in that the resolution is performed at a very early stage of the synthesis, preferably on a hemi-acetal intermediate. In the present method, the undesired menthol diastereomer can be separated out and recycled. Thus, in principle, the hemi-acetal intermediate is transformed to a single diastereomer.

In carrying out the method of the invention, referring to the above reaction sequence, the racemic cis-exo or cis-endo hemiacetal

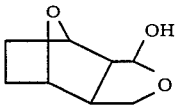

is converted to a diastereomeric mixture of menthol compounds III (or V) and II (or VI) by reacting same with l-menthol in the presence of trace amounts of p-toluenesulfonic acid and an inert solvent such as benzene at reflux temperatures under an inert atmosphere, for example, nitrogen to form a mixture of diastereomers of formula II or III (or V or VI) which is recrystallized, for example, from methylene chloride-ethyl acetate and thus resolved to form the optically active acetal isomer II or III

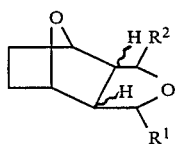

(where one of $R^1$ and $R^2$ is —O—menthol and the other is H).

The acetal II or III (or V or VI) is allowed to react with benzyl alcohol at elevated temperatures of at least 110° to form the optically active benzyloxy compound

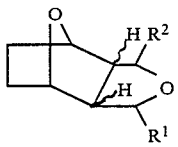

IV (wherein one of $R^1$ and $R^2$ is benzyloxy and the other is H) which is subjected to a hydrogenolysis reaction, for example, by reaction with hydrogen in the presence of palladium on charcoal to form the optically active hemiacetal

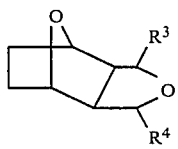

J (wherein one of $R^3$ and $R^4$ is OH and the other is H).

As indicated, replacement of the l-menthol compound with the corresponding d-isomer in the reaction sequence produces, instead of the optically active (−) antipodes II or III or V or VI, the corresponding optically active (+) antipodes.

The hemiacetal J may then be employed to form optically active hemiacetal L by subjecting hemiacetal J to a homologation reaction, for example, by submitting J to Wittig reaction conditions by reacting J with an (alkoxymethyl)triphenylphosphonium halide such as (methoxymethyl)triphenylphosphonium chloride in the presence of an alkylamine like diisopropylamine, a lithium alkyl like n-butyl lithium in an inert organic medium like hexane, tetrahydrofuran or the like, at a temperature in the range of about −10° to 25° C. to form optically active compound K

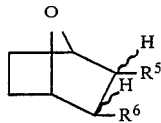

(wherein one of $R^5$ and $R^6$ is $CH_2OH$ and the other is —CH=CH—OCH$_3$).

Hydrolysis of alcohol compound K in the presence of strong acid such as trifluoroacetic acid produces optically active hemi-acetal L which is then subjected to Wittig reaction conditions and esterification, for example, reaction with a carboxyalkyl triphenylphosphonium halide, such as, triphenylcarboxybutylphosphonium chloride, in the presence of inert solvent, such as DMSO, to form optically an active alcohol which is then reacted with, for example, a diazoalkane like diazomethane, to form the alcohol ester M

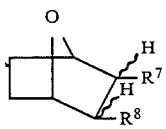

(wherein one of $R^7$ and $R^8$ is —CH$_2$—CH=CH— lower alkylene $CO_2CH_3$ and the other is —CH$_2$OH).

The optically active alcohol ester M may then be oxidized, for example, by reaction with chromium oxide with pyridine to form the optically active aldehyde N.

Thus, it is seen that the aldehyde N may be prepared from the starting hemiacetal without recourse to any chromatographic purification.

The prostaglandin aldehyde analog N may then be employed to prepare 7-oxabicycloheptane prostaglandins following the procedure as set out in U.S. Pat. No. 4,143,054 to Sprague. Such prostaglandin derivatives are useful in the treatment of thrombolytic disease as explained in the above Sprague patent.

The wavy line ($\sim\!\sim$) which serves as a linking group for hydrogen in many of the formulae set out herein refers to the fact that the hydrogen atom may be cis exo or cis endo to the oxa bridge.

The nucleus in each of the compounds of the invention is depicted as

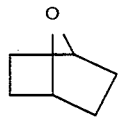

for matter of convenience; it will also be appreciated that the nucleus in the compounds of the invention may be depicted as

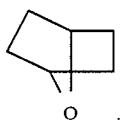

The following Examples represent preferred embodiments of the present invention.

EXAMPLES 1 AND 2

[3aS-[1-(1R,2S,5R),3aα,4α,7α,7aα]]-Octahydro-1-[[5-methyl-2-(1-methylethyl)-cyclohexyl]oxy]-4,7-epoxyisobenzofuran (Isomer I, Example 1) and
[3aR-[1-(1R,2S,5R),3aα,4α,7α,7aα]]-Octahydro-1-[[5-methyl-2-(1-methylethyl)cyclohexyl]oxy]-4,7-epoxyisobenzofuran (Isomer II, Example 2)

A solution of (exo)-octahydro-4,7-epoxyisobenzofuran-1-ol prepared as described in U.S. Pat. No. 4,143,054 (21 g, 0.13 mole), levo-menthol (21 g, 0.13 mole) and p-toluenesulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10 g of [3aR-[1-(1R,2S,5R),3aα,4α,7α,7aα]]-octhydro-1-[[5-methyl-2-(1-methylethyl)cyclohexyl]oxy]-4,7-epoxyisobenzofuran (pure isomer II), m.p. 109°–111° C. The mother liquor was concentrated to 100 ml then treated with water to yield 10 g of solid which contained approximately 90% isomer I, that is [3aS-[1-(1R,2S,5R),3aα,4α,7α,7aα]]-octahydro-1-[[5-methyl-2-(1-methylethyl)cyclohexyl]oxy]-4,7-epoxyisobenzofuran and 10% isomer II by C-13 NMR. The mixture was recrystallized from pentane (100 ml) at −40° C. to yield (after four recrystallizations) 8 g of product containing ~5% isomer II and 95% isomer I.

TLC: silica gel: ether/hexane; $R_f$=0.35; vanillin spray and heat.

EXAMPLES 3 AND 4

[3aS-(3aα,4α,7α,7aα)]-Octahydro-1-benzyloxy-4,7-epoxyisobenzofuran (Example 3 Isomer A) and
[3aR-(3aα,4α,7α,7aα)]-Octahydro-1-benzyloxy-4,7-epoxyisobenzofuran (Example 4 Isomer B)

A solution of isomer II [3aR-[1-(1R,2S,5R),3aα,4α,7α,7aα]]-octahydro-1-[[5-methyl-2-(1-methylethyl)cyclohexyl]oxy]-4,7-epoxy-isobenzofuran (from Example 2) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of isomer A, an oil, and 7.8 g of isomer B, m.p. 47°–50° C. These isomers appeared to be positional isomers of the benzyloxy group about the carbon atom.

TLC of isomer A: silica gel; hexane/ether (1:1), $R_f$=0.25; vanillin spray and heat.

TLC of isomer B: silica gel; hexane/ether (1:1), $R_f$=0.2; vanillin spray and heat.

EXAMPLE 5

[1R-(1α,2β(5Z),3β,4α)-7-[3-Formyl-7-oxabicyclo[2.2.1]hept-2-yl]-5-heptanoic acid, methyl ester

A.
[3aS-(3aα,4α,7α,7aα)]-Octahydro-4,7-epoxyisobenzofuran-1-ol

A mixture of isomer a (prepared as described in Example 3) (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C.

$[α]_D$= −44°, $[α]_{365}{}^{Hg}$= −122°, c=10 mg/ml MeOH.
TLC: silica gel; ethyl acetate/dichloromethane (1:1), $R_f$=0.2; vanillin spray and heat.

B.
[1R-(1α,2β,3β,4α)]-3-(Hydroxymethyl)-2-(2-methoxyethenyl)-7-oxabicyclo[2.2.1]heptane A slurry of methoxymethyltriphenylphosphonium chloride (28.1 g, 0.082 mole) in toluene (700 ml) was treated with a solution of lithium diisopropylamide (prepared from 1.6M n-butyl lithium (51 ml, 0.082 mole) and diisopropylamine (14.25 ml, 0.10 mole) in pentane) in tetrahydrofuran (20 ml). The mixture was stirred at room temperature for 30 minutes then treated with title A compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether to yield the desired title B product contaminated with phosphine oxide. This product was distilled in vacuo to yield 3 g of title B compound, b.p. 90° C./0.01 mm.

$[α]_D$= +44°, $[α]_{365}{}^{Hg}$= +138°, c=11 mg/ml MeOH.
TLC: silica gel; ethyl acetate/dichloromethane (1:1); $R_f$=0.2; vanillin spray and heat.

C.
[4aS-(4aα,5α,8α,8aα)]-Octahydro-5,8-epoxy-(1H)-benzopyran-3-ol

A solution of title B compound (3g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title C compound, m.p. 104°–105° C.

$[α]_D$= +27.2°, $[α]_{365}{}^{Hg}$=0, c=7.9 mg/ml MeOH.

D.
[1R-[1α,2β(5Z),3β,4α]]-7-[3-(Hydroxymethyl)-7-oxabicyclo[2.2.1]hept-2-yl]-5-heptenoic acid and

E.
[1R-[1α,2β(5Z),3β,4α]]-7-[3-(Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes then treated with title C compound (2.4 g, 0.0141 mole). The reaction mixture was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate containing title D acid was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title E compound.

$[α]_D = +11.2°$, $[α]_{365}^{Hg}=0$, c—16.9 mg/ml MeOH.

TLC: silica gel; ether; $R_f=0.4$; vanillin spray and heat.

F.
[1R-[1α,2β(5Z),3β,4α]]-7-[3-Formyl-7-oxabicyclo[2.2.1]hept-2-yl]-5-heptenoic acid, methyl ester A solution of pyridine (10.75 ml, 0.133 mole) in anhydrous dichloromethane (350 ml) was treated portionwise with chromium trioxide (6.68 g, 0.067 mole) then stirred vigorously at room temperature for 30 minutes. The red mixture was then treated with dry celite (20 g) followed by title E compound (3 g, 0.0113 mole) dissolved in dichloromethane (20 ml). The mixture was stirred at room temperature for 30 minutes then filtered through celite. The filtrate was washed with 5% sodium bicarbonate (3×100 ml), 10% hydrochloric acid (2×250 ml), 5% sodium bicarbonate (1×200 ml), dried over magnesium sulfate, and concentrated in vacuo. The residue was dissolved in ether, treated with carbon and filtered. The filtrate was concentrated in vacuo to yield 2.9 g of title aldehyde.

TLC: silica gel; hexane/ether (1:1); $R_f=0.5$; vanillin spray and heat.

EXAMPLES 6 AND 7

[3aS-[1-(1R,2S,5R),3aα,4β,7β,7aα]]-Octahydro-1-[[5-methyl-2-(1-methylethyl)cyclohexyl]oxy]-4,7-epoxyisobenzofuran (Isomer I, Examle 6) and
[3aR-[1-(1R,2S,5R),3aα,4β,7β,7aα]]-Octahydro-1-[[5-methyl-2-(1-methylethyl)cyclohexyl]oxy]-4,7-epoxyisobenzofuran (Isomer II, Example 7)

A mixture of (endo)-octahydro-4,7-epoxyisobenzofuran-1-ol (prepared as described in U.S. Pat. No. 4,143,054) (26.6 g, 0.17 mole), 1-menthol (26.6 g, 0.17 mole) and p-toluenesulfonic acid (trace) was prepared in benzene (1400 ml). This mixture was heated at reflux for 18 hours under $N_2$ with a Dean-Stark trap containing molecular sieves in the system. The mixture was cooled, washed with 5% $NaHCO_3$ (500 ml) and concentrated yielding crystalline crude material. This was dissolved in hot MeOH (900 ml) and allowed to cool. Example 6 (Isomer I) compound (20.5 g) crystallized out first and concentration of the filtrate to 500 ml yielded an additional 2 g of Example 6 compound for a total of 22.5 g, m.p. 160°–162°. Isomer II (Example 7) was obtained by further concentrations of the mother liquor removing small amounts of mixed samples containing isomer I. When the percentage of I in the residue was >10% (as estimated by C-13 NMR) recrystallization of this from MeOH gave 17.8 g of pure Isomer II, m.p. 88°–90° C.

EXAMPLE 8

[3aS-(3aα,4β,7β,7aα)]-Octahydro-1-benzyloxy-4,7-epoxyisobenzofuran

A mixture of Example 6 Isomer I compound (10 g, 0.034 mole) and p-toluenesulfonic acid (trace) was prepared in benzyl alcohol (100 ml) and heated to 120° for 4 hours. The mixture was cooled and partitioned between water and hexane. The hexane layer was washed with water (4×500 ml), treated with Norite, dried ($MgSO_4$) and concentrated to yield crude title compound which was recrystallized from EtOAc to yield 8.3 g of title benzyl acetal compound, m.p. 108°–110°.

EXAMPLE 9

[1S-[1α,2α(5Z)3α,4α]]-7-[3-Formyl-7-oxabicyclo[2.2.1]hept-2-yl]-5-heptenoic acid, methyl ester

A.
[3aS-(3aα,4β,7β,7aα)]-Octahydro-4,7-epoxyisobenzofuran-1-ol

A mixture of Example 8 compound (18.03 g, 73.3 mmole) and 10% palladium on charcoal (1.8 g) was prepared in ethyl acetate (200 ml) and hydrogenated at atmospheric pressure until 1 mole of $H_2$ had been consumed (~1 hour, 1641 ml). The catalyst was removed by filtration and, after concentration of the filtrate, 11.5 g of crystalline title hemiacetal m.p. 120°–130° was obtained. Recrystallization from cyclohexane-benzene yielded 10.2 g of title A compound, m.p. 132° $[α]_D= -79°$. C=10 mg/ml, MeOH.

B.
[1S-(1α,2α,3α,4α)]-2-(2-Methoxyethenyl)-3-hydroxymethyl-7-oxabicyclo[2.2.1]heptene Lithium diisopropylamide (from 96 mmole of n-butyl Li (1.6 mmole/ml) in hexane and 120 mmole of diisopropylamine (16.8 ml)) was prepared under anhydrous conditions and dissolved in dry THF (20 ml). This was added to a mixture of triphenylmethoxymethylphosphonium chloride (33 g, 96 mmole) and dry toluene (450 ml) at 0° under argon with mechanical stirring. After stirring the resulting red ylide (nearly everything dissolved) for 30 minutes at 0°, the title A hemiacetal (5.0 g, 32 mmole) in powdered form was added via a solids addition device and the resulting mixture stirred at 20° for 5 hours. The reaction was quenched by addition of HOAc (96 mmole) and poured into brine (1 L). This was extracted with ether (3×300 ml), the extracts dried (MgSO$_4$) and concentrated to yield an oil. Purification by flash chromatography on LP-1 silica gel (500 ml) eluting with 50/50 ether/pentane to start and finishing with ether gave 4.8 g of enolether which on distillation (b.p. 107°–112° @ 0.001 mm) gave 3.8 g of pure enolether containing ~5% (by NMR) unchanged title B compound.

C.
[4aS-(4aα,5β,8β,8aα)]-Octahydro-5,8-epoxy-(1H)-benzopyran-3-ol

A mixture of crude title B compound (containing ~5% title B compound) (6.1 g) and trifluoroacetic acid (20% in H$_2$O, 100 ml) was prepared and rapidly stirred under argon at 25° for 2 hours. The acid was decomposed with solid NaHCO$_3$, and the neutral mixture saturated with salt and extracted with CH$_2$Cl$_2$ (6×300 ml). The extracts were dried (MgSO$_4$) and concentrated to yield an oil which contains significant amounts of partial hydrolysis products. This material was subjected to a second treatment with TFA as above and after a second work up yielded 5.7 g of product which consisted of title C compound contaminated with title B compound. These two materials were separated by flash chromatography on LP-1 silica gel (600 ml) using 70/30 ether/pentane as the eluent. Yield of pure title C compound 3.75 g [α]$_D$=+15°. C=8.3 mg/ml, MeOH.

D.
[1S-[1α,2α(5Z),3α,4α]]-7-[3-(Hydroxymethyl)-7-oxabicyclo[2.2.1]hept-2-yl]-5-heptenoic acid and

E.
[1S-[1α,2α(5Z),3α,4α]]-7-[3-(Hydroxymethyl)-7-oxabicyclo[2.2.1]hept-2-yl]-5-heptenoic acid, methyl ester A mixture of triphenylcarboxybutylphosphonium ylide was prepared in dry DMSO (60 ml) from triphenylcarboxybutylphosphonium bromide (29.3 g, 66 mmole) and freshly prepared dimsyl ion at 25° under argon. To this was added title C compound (3.75 g, 22 mmole) dissolved in DMSO (10 ml) and the resulting mixture stirred at 25° for 2 hours. The mixture was quenched by HOAc (66 mmole) in ether (5 ml) and then poured into brine (1 L) and extracted with EtOAc (4×300 ml). The extracts were dried (MgSO$_4$) and concentrated to yield and oil which was shaken with saturated NaHCO$_3$ to separate acidic products from triphenylphosphine oxide. This mixture was extracted with benzene (3×100 ml) followed by EtOAc (3×100 ml) then acidified to pH 2 with concentrated HCl and extracted with ether (6×200 ml). The combined extracts were dried (MgSO$_4$) and chilled whereupon a crystalline material appeared. This was removed after 24 hours and the filtrate concentrated to yield 4.0 g of crude acid title D acid. The acid was esterified directly by treatment in ether with excess diazomethane at 25°. Title E ester was purified by flash column chromatography on LP-1 silica gel (500 ml) eluting with 50/50 hexane/ether followed by ether to yield 2.91 g of title E ester [α]$_{Hg,365}$=−23° C=12.5 mg, MeOH. (TLC R$_f$=0.6, silica gel EM, ether, spot visualization with PMA+H$^⊕$+Δ).

F.
[1S-[1α,2α(5Z),3α,4α]]-7-[3-Formyl-7-oxabicyclo[2.2.1]hept-2-yl]-5-heptenoic acid, methyl ester A mixture of chromium oxide (6.48 g, 6.48 mmole), pyridine (10.4 ml, 129.6 mmole) and CH$_2$Cl$_2$ (340 ml) was prepared and stirred at 25° for 30 minutes under argon. Dry celite (18 g) was added followed by title E ester (2.91 g, 10.8 mmole) dissolved in CH$_2$Cl$_2$ (15 ml) and stirring was continued for 30 minutes. The mixture was filtered and the filtrate washed with 5% NaHCO$_3$ (3×100 ml), 5% NaHSO$_4$ (2×250 ml), 5% NaHCO$_3$ (1×200 ml), dried (MgSO$_4$) and concentrated. The residue was dissolved in ether, treated with Norite, filtered and concentrated to yield 2.6 g of title aldehyde.

EXAMPLES 10 AND 11

[3aS-[1-(1S,2R,5S),3aα,4α,7α,7aα]]-Octahydro-1-[[5-methyl-2-(1-methylethyl)cyclohexyl]oxy]-4,7-epoxyisobenzofuran (Example 10, Isomer I) and
[3aR-[1-(1S,2R,5S),3aα,4α,7α,7aα]]-Octahydro-1-[[5-methyl-2-(1-methylethyl)cyclohexyl]oxy]-4,7-epoxyisobenzofuran (Example 11, Isomer II)

Following the procedure of Examples 1 and 2 except substituting d-menthol for l-menthol, the title compounds are obtained.

EXAMPLES 12 AND 13

[3aR-(3aα,4α,7α,7aα)]-Octahydro-1-benzyloxy-4,7-epoxyisobenzofuran (Example 12, Isomer A) and
[3aS-[3aα,4α,7α,7aα)]-Octahydro-1-benzyloxy-4,7-epoxyisobenzofuran (Example 13, Isomer B)

Following the procedure of Examples 3 and 4 except substituting the Example 11, Isomer II compound for the Example 2, Isomer II compound, the title compounds are obtained.

EXAMPLE 14

[3aR-(3aα,4α,7α,7aα)]-7-[3-Formyl-7-oxabicyclo[2.2.1]hept-2-yl]-5-heptenoic acid, methyl ester Following the procedure of Example 5 except substituting the Example 12, Isomer A compound for the Example 3, Isomer A compound, the title aldehyde is obtained.

EXAMPLE 15 AND 16

[3aS-[1-(1S,2R,5S),3aα,4β,7β,7aα]]-Octahydro-1-[[5-methyl-2-(1-methylethyl)cyclohexyl]oxy]-4,7-epoxyisobenzofuran (Example 15, Isomer I) and
[3aR-[1-(1S,2R,5S),3aα,4β,7β,7aα]]-Octahydro-1-[[5-methyl-2-(1-methylethyl)cyclohexyl]oxy]-4,7-epoxyisobenzofuran (Example 16, Isomer II)

Following the procedure of Examples 6 and 7 except substituting d-menthol for l-menthol, the title compound are obtained.

EXAMPLE 17

[3aR-(3aα,4β,7β,7aα)]-Octahydro-1-benzyloxy-4,7-epoxyisobenzofuran

Following the procedure of Example 8 except substituting the Example 16, Isomer II compound for the Example 6, Isomer I compound, the title compound is obtained.

EXAMPLE 18

[1R-[1α,2α(5Z),3α,4α]]-7-[3-Formyl-7-oxabicyclo[2.2.1]hept-2-yl]-5-heptenoic acid, methyl ester Following the procedure of Example 9 except substituting the Example 17 compound for the Example 8 comound, the title compound is obtained.

What is claimed is:

1. A compound having the structure

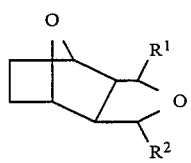

wherein one of R¹ and R² is

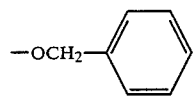

and the other is hydrogen.

2. The compound as defined in claim 1 wherein R¹ is H and R² is

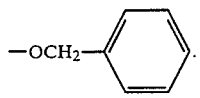

3. The compound as defined in claim 1 wherein R² is H and R¹ is

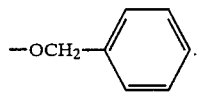

4. The compound as defined in claim 1 having the formula

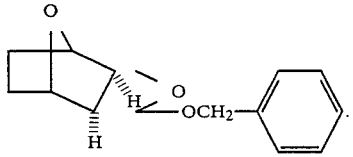

5. The compound as defined in claim 1 having the formula

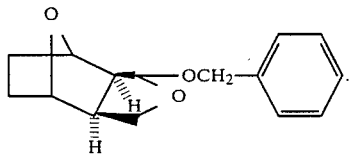

6. The compound as defined in claim 1 having the formula

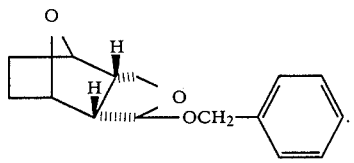

7. The compound as defined in claim 1 having the formula

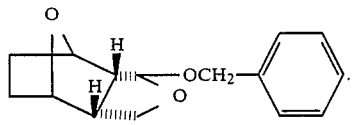

8. An optically active cis endo or cis exo isomer having the structure

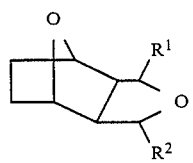

wherein one of R¹ and R² is

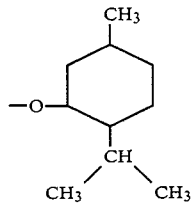

and the other is hydrogen.

9. The compound as defined in claim 8 wherein R¹ is H and R² is

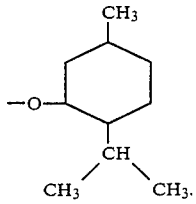

10. The compound as defined in claim 8 wherein R² is H and R¹ is

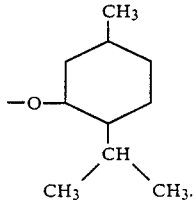

11. The compound as defined in claim 8 having the formula

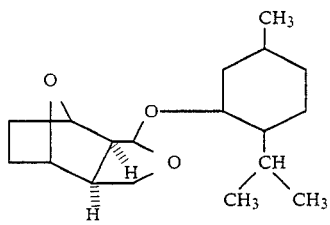

(−) or (+)

cis exo.

12. The compound as defined in claim 8 having the formula

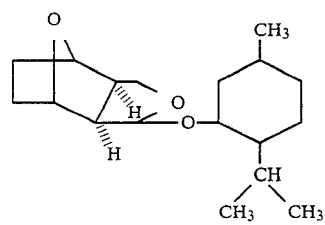

(−) or (+)

cis exo.

13. The compound as defined in claim 8 having the formula

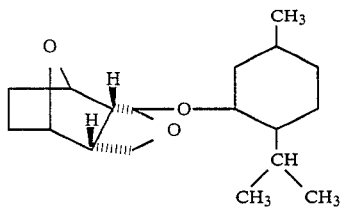

(−) or (+)

cis endo.

14. The compound as defined in claim 8 having the formula

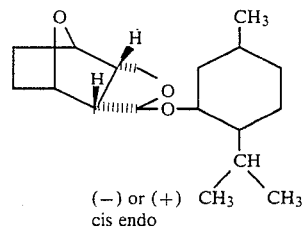

(−) or (+)
cis endo

15. A method for preparing compounds as defined in claim 1 which comprises etherifying a hemiacetal of the formula

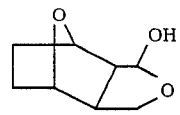

by reacting same with d or l-menthol to form a mixture of diastereomers, crystallizing the above mixture to resolve same and recover optically active diastereomer of the structure

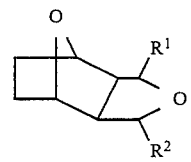

wherein one of $R^1$ and $R^2$ is

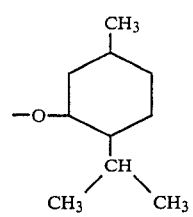

and the other is H, and reacting the above hemiacetal with benzyl alcohol to form the optically active compound

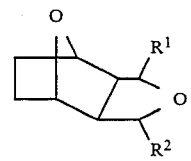

wherein one of $R^1$ and $R^2$ is

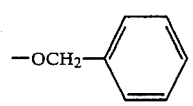

and the other is H.

* * * * *

UNITED STATES PATENT AND TRADEMARK OFFICE
CERTIFICATE OF CORRECTION

PATENT NO. : 4,499,292
DATED : February 12, 1985
INVENTOR(S) : Peter W. Sprague et al.

It is certified that error appears in the above—identified patent and that said Letters Patent is hereby corrected as shown below:

Column 3, structure III should read

III 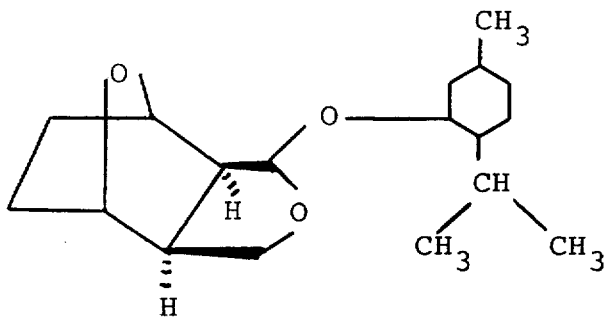

Column 3, structure IV should read

IV 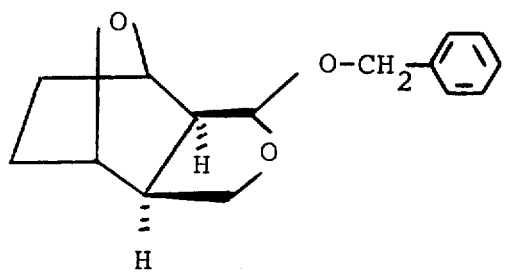

UNITED STATES PATENT AND TRADEMARK OFFICE
CERTIFICATE OF CORRECTION

PATENT NO. : 4,499,292
DATED : February 12, 1985
INVENTOR(S) : Peter W. Sprague et al.

It is certified that error appears in the above—identified patent and that said Letters Patent is hereby corrected as shown below:

Column 3, structure IVa should read

IVa
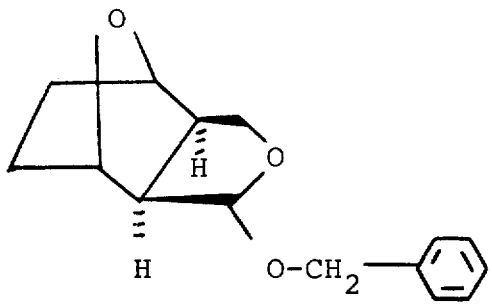

Column 10, line 4, "heptanoic" should read --heptenoic--.
Column 10, line 9, "isomer a" should read --isomer A--.
Column 13, line 56, "and" should read --an--.

Signed and Sealed this

Fifteenth Day of October 1985

[SEAL]

Attest:

DONALD J. QUIGG

Attesting Officer

Commissioner of Patents and Trademarks—Designate